(12) United States Patent
Hardie et al.

(10) Patent No.: US 11,478,387 B2
(45) Date of Patent: Oct. 25, 2022

(54) FOLDED DISPOSABLE ABSORBENT ARTICLES

(71) Applicant: The Procter & Gamble Company, Cincinnati, OH (US)

(72) Inventors: Stephen Lebeuf Hardie, Mason, OH (US); Ronda Lynn Glassmeyer, Harrison, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 652 days.

(21) Appl. No.: 16/381,662

(22) Filed: Apr. 11, 2019

(65) Prior Publication Data

US 2019/0314219 A1 Oct. 17, 2019

Related U.S. Application Data

(60) Provisional application No. 62/656,022, filed on Apr. 11, 2018.

(51) Int. Cl.
*A61F 13/535* (2006.01)
*A61F 13/15* (2006.01)
(Continued)

(52) U.S. Cl.
CPC ...... *A61F 13/535* (2013.01); *A61F 13/15203* (2013.01); *A61F 13/15658* (2013.01); *A61F 13/511* (2013.01); *A61F 13/514* (2013.01); *A61F 13/534* (2013.01); *A61L 15/60* (2013.01); *A61F 13/475* (2013.01); *A61F 13/494* (2013.01);
(Continued)

(58) Field of Classification Search
CPC ............ A61F 13/4704; A61F 13/49001; A61F 13/534; A61F 13/535; A61F 13/55315; A61F 13/5514; A61F 13/53409; A61F 13/53418; A61F 13/53427;
(Continued)

(56) References Cited

U.S. PATENT DOCUMENTS 1,946,626 A 2/1934 Jurgensen
2,296,341 A 9/1942 Fourness
(Continued)

FOREIGN PATENT DOCUMENTS

CN 202960948 U 6/2013
EP 0631768 A1 1/1995
(Continued)

OTHER PUBLICATIONS

U.S. Appl. No. 16/381,084, filed Apr. 11, 2019, Busch et al.
(Continued)

*Primary Examiner* — Catharine L Anderson
*Assistant Examiner* — Lynne Anderson
(74) *Attorney, Agent, or Firm* — William E. Gallagher; George H. Leal

(57) ABSTRACT

Disposable absorbent articles are disclosed herein having a first and second fold line. The disposable absorbent articles have a topsheet, a backsheet, and an absorbent system disposed therebetween. The absorbent system has a first absorbent core and a second absorbent core which may be configured in an offset manner. And, the absorbent system and/or the first and second fold lines may be configured with respect to the absorbent article to effect a caliper change in the folded article.

18 Claims, 10 Drawing Sheets

(51) Int. Cl.
  *A61F 13/511* (2006.01)
  *A61F 13/514* (2006.01)
  *A61F 13/534* (2006.01)
  *A61L 15/60* (2006.01)
  *A61F 13/53* (2006.01)
  *A61F 13/475* (2006.01)
  *A61F 13/494* (2006.01)

(52) U.S. Cl.
  CPC ............. A61F 2013/15373 (2013.01); A61F 2013/15569 (2013.01); A61F 2013/53024 (2013.01); A61F 2013/530481 (2013.01); A61F 2013/530868 (2013.01); A61F 2013/530927 (2013.01)

(58) Field of Classification Search
  CPC .. A61F 2013/15365; A61F 2013/53445; A61F 2013/5355
  See application file for complete search history.

(56) References Cited

U.S. PATENT DOCUMENTS

| | | |
|---|---|---|
| 3,386,442 A | 6/1968 | Reinhardt |
| 3,406,688 A | 10/1968 | Cubitt |
| 3,431,911 A | 3/1969 | Meisel, Jr. |
| 3,528,421 A | 9/1970 | Vaillancourt |
| 3,572,342 A | 3/1971 | Lindquist |
| 3,604,422 A | 9/1971 | Sabee |
| 3,651,809 A | 3/1972 | Champaigne, Jr. |
| 3,695,269 A | 10/1972 | Malaney |
| 3,799,167 A | 3/1974 | Miller et al. |
| 3,805,790 A | 4/1974 | Kaczmarzyk |
| 3,815,602 A | 6/1974 | Johns et al. |
| 3,825,006 A | 7/1974 | Ralph |
| 3,838,693 A | 10/1974 | Sherman |
| 3,848,599 A * | 11/1974 | Schaar .............. A61F 13/51476 604/385.23 |
| 3,871,037 A | 3/1975 | Willington |
| 3,878,283 A | 4/1975 | Jones, Sr. |
| 3,954,721 A | 5/1976 | Gross |
| 3,983,095 A | 9/1976 | Bashaw et al. |
| 3,996,936 A | 12/1976 | Widlund et al. |
| 4,047,531 A | 9/1977 | Karami |
| 4,102,340 A | 7/1978 | Mesek et al. |
| 4,136,697 A | 1/1979 | Smith |
| 4,211,227 A | 7/1980 | Anderson et al. |
| 4,231,357 A | 11/1980 | Hessner |
| 4,269,188 A | 5/1981 | Nishizawa et al. |
| 4,285,342 A | 8/1981 | Mesek |
| 4,333,464 A | 6/1982 | Nakano |
| 4,333,465 A | 6/1982 | Wiegner |
| 4,335,722 A | 6/1982 | Jackson |
| 4,338,371 A | 7/1982 | Dawn et al. |
| 4,354,901 A | 10/1982 | Kopolow |
| 4,364,992 A | 12/1982 | Ito et al. |
| 4,381,783 A | 5/1983 | Elias |
| 4,397,644 A | 8/1983 | Matthews et al. |
| 4,410,324 A | 10/1983 | Sabee |
| 4,411,660 A | 10/1983 | Dawn et al. |
| 4,480,000 A | 10/1984 | Watanabe |
| 4,500,315 A | 2/1985 | Iskra |
| 4,536,181 A * | 8/1985 | Cook .................... A61F 13/474 604/387 |
| 4,537,590 A | 8/1985 | Iskra |
| 4,557,777 A | 12/1985 | Sabee |
| 4,560,372 A | 12/1985 | Pieniak |
| 4,560,379 A | 12/1985 | Stemmler |
| 4,610,678 A | 9/1986 | Weisman |
| 4,655,757 A | 4/1987 | Mcfarland |
| 4,666,439 A | 5/1987 | Williams |
| 4,673,402 A | 6/1987 | Weisman et al. |
| 4,676,784 A | 6/1987 | Erdman |
| 4,685,914 A | 8/1987 | Holtman |
| 4,699,823 A | 10/1987 | Kellenberger |
| 4,710,187 A | 12/1987 | Boland |
| 4,762,521 A | 8/1988 | Roessler et al. |
| 4,770,656 A | 9/1988 | Proxmire |
| 4,781,711 A | 11/1988 | Houghton et al. |
| 4,790,839 A | 12/1988 | Ahr |
| 4,798,603 A | 1/1989 | Meyer |
| 4,806,408 A | 2/1989 | Pierre et al. |
| 4,888,093 A | 12/1989 | Dean |
| 4,888,238 A | 12/1989 | Katz |
| 4,900,318 A | 2/1990 | Toth |
| 4,911,700 A | 3/1990 | Makoui |
| 4,923,454 A | 5/1990 | Seymour |
| 4,935,022 A | 6/1990 | Lash et al. |
| 4,944,735 A | 7/1990 | Mokry |
| 4,973,325 A | 11/1990 | Sherrod et al. |
| 4,988,344 A | 1/1991 | Reising et al. |
| 4,988,345 A | 1/1991 | Reising |
| 4,990,147 A | 2/1991 | Freeland |
| 5,009,650 A | 4/1991 | Bernardin |
| 5,013,309 A | 5/1991 | Baigas, Jr. et al. |
| 5,037,409 A | 8/1991 | Wisneski |
| 5,061,259 A | 10/1991 | Goldman |
| 5,061,260 A | 10/1991 | Callahan |
| 5,069,676 A | 12/1991 | Ito |
| 5,079,004 A | 1/1992 | Blank |
| 5,087,506 A | 2/1992 | Palumbo |
| 5,098,422 A | 3/1992 | Davis |
| 5,134,007 A | 7/1992 | Reising et al. |
| 5,147,343 A | 9/1992 | Kellenberger |
| 5,147,345 A | 9/1992 | Lavon |
| 5,149,335 A | 9/1992 | Kellenberger |
| 5,176,668 A | 1/1993 | Bernardin |
| 5,192,606 A | 3/1993 | Proxmire |
| 5,294,478 A | 3/1994 | Wanek et al. |
| 5,300,053 A | 4/1994 | Genaro |
| 5,300,054 A | 4/1994 | Feist |
| 5,304,161 A | 4/1994 | Noel et al. |
| 5,387,207 A | 2/1995 | Dyer |
| 5,411,497 A | 5/1995 | Tanzer |
| 5,425,725 A | 6/1995 | Tanzer |
| 5,433,715 A | 7/1995 | Tanzer |
| 5,440,061 A | 8/1995 | Gibson |
| 5,454,800 A | 10/1995 | Hirt et al. |
| 5,466,513 A | 11/1995 | Wanek |
| 5,509,915 A | 4/1996 | Hanson |
| 5,830,202 A | 11/1998 | Bogdanski et al. |
| 5,853,402 A * | 12/1998 | Faulks .............. A61F 13/53713 604/378 |
| 6,068,620 A | 5/2000 | Chmielewski |
| 7,686,792 B2 * | 3/2010 | Bell ...................... A61F 13/474 604/385.16 |
| 8,702,671 B2 * | 4/2014 | Tsang .................... A61F 13/533 604/385.21 |
| 9,238,089 B2 | 1/2016 | Chmielewski et al. |
| 2003/0225384 A1 | 12/2003 | Zenker et al. |
| 2004/0015142 A1 | 1/2004 | Johnston et al. |
| 2006/0018415 A1 | 1/2006 | Jung |
| 2006/0069367 A1 | 3/2006 | Waksmundzki et al. |
| 2011/0028927 A1* | 2/2011 | Bellucci ................. A61F 13/60 604/365 |
| 2012/0043244 A1 | 2/2012 | Hagner |
| 2012/0053547 A1 | 3/2012 | Schroeder |
| 2012/0292224 A1 | 11/2012 | Matsushima et al. |
| 2014/0005623 A1 | 1/2014 | Wirtz et al. |
| 2014/0163500 A1 | 6/2014 | Roe |
| 2014/0213997 A1 | 7/2014 | Tsang |
| 2016/0235602 A1 | 8/2016 | Ehmsperger |
| 2017/0312146 A1 | 11/2017 | Bianchi |
| 2020/0060887 A1* | 2/2020 | Vartiainen ......... A61F 13/55135 |

FOREIGN PATENT DOCUMENTS

| | | |
|---|---|---|
| EP | 2594238 A2 | 5/2013 |
| EP | 2901992 B1 | 12/2016 |
| EP | 3205318 A1 | 8/2017 |
| GB | 1259865 A | 1/1972 |
| WO | WO9962801 A2 | 12/1999 |
| WO | 0076447 A1 | 12/2000 |

(56) References Cited

FOREIGN PATENT DOCUMENTS

| WO | WO2005060892 A1 | 7/2005 |
| WO | 2013180937 A1 | 12/2013 |
| WO | 2014145804 A1 | 9/2014 |
| WO | 2015188032 A1 | 12/2015 |

OTHER PUBLICATIONS

U.S. Appl. No. 16/381,251, filed Apr. 11, 2019, Hardie et al.
U.S. Appl. No. 16/381,075, filed Apr. 11, 2019, Busch et al.
Search Report and Written Opinion for PCT/US2019/026934 dated Jun. 25, 2019.
PCT Search Report and Written Opinion for PCT/US2019/026935 dated Jul. 4, 2019.
Search Report and Written Opinion for PCT/US2019/026971 dated Jun. 25, 2019.
Search Report and Written Opinion for PCT/US2019/026905 dated Jun. 25, 2019.
All Office Actions for U.S. Appl. No. 16/381,084, filed Apr. 11, 2019.
All Office Actions for U.S. Appl. No. 16/381,251, filed Apr. 11, 2019.
All Office Actions for U.S. Appl. No. 16/381,075, filed Apr. 11, 2019.

\* cited by examiner

FOLDED DISPOSABLE ABSORBENT ARTICLES

FIELD

The present invention pertains to folded disposable absorbent articles suitable for absorbing and containing body exudates.

BACKGROUND

A variety of disposable absorbent articles have been relied on by consumers to handle or manage body exudates. These consumers may include babies, toddlers, children, teenagers, adults, and elderly persons. Thus, it is clear that the types of fluids or body exudates managed by such articles may vary as well to include urine, feces, menses, and other discharges. Typically, in the case of adults, the articles take the form of sanitary napkins, adult incontinence pads, and adult incontinence diapers or undergarments. One of the primary drivers of the desirability of these products to wearers is to give them assurance that when they experience incontinence, the occurrence of such will go unnoticed by others and even more ideally by the wearers.

One way of improving the performance and overall discretion of disposable absorbent articles that has been widely utilized by manufacturers has been the inclusion of superabsorbent polymers which are able to intake increased amounts of liquid and consequently form a swollen hydrogel material. The resulting hydrogel serves to retain fluid such as discharged body liquids within the structure. An absorbent structure of this type wherein hydrogel-forming materials in particulate form are incorporated into fibrous webs is disclosed in Weisman and Goldman; U.S. Pat. No. 4,610,678; issued Sep. 9, 1986.

While disposable absorbent articles with these superabsorbent materials tend to be highly absorbent and less bulky, there are a number of users of these products that have a high body mass index (BMI) for which these products still leave much to be desired. In particular, these users tend to experience exaggerated bunching of the absorbent article during wear and as a result there can be increased opportunity for leaks to occur.

Consequently, there is a need for a disposable absorbent article which targets to provide increased protection from leakage to consumers which have a high BMI while maintaining a level of discretion to the wearer while in use. Additionally, there is a need to provide the disposable absorbent article in discreet packaging with a generally small foot print.

SUMMARY

Disposable absorbent articles in accordance with the present disclosure are well suited for providing leakage protection for users that experience relatively small to relatively large discharges of fluids. Additionally, the disposable absorbent article of the present disclosure can be folded in a variety of ways to impact the resulting caliper of the pads.

An exemplary array of disposable absorbent articles, wherein each of the absorbent articles within the array comprises a front end portion an opposing second end portion, and an intermediate portion disposed between the front end portion and the second end portion, the array further comprising: a first plurality of absorbent articles and a second plurality of absorbent articles, each of the first plurality of absorbent articles and second plurality of absorbent articles comprising: a topsheet, a backsheet, and an absorbent system disposed between the topsheet and the backsheet, the absorbent system comprising a first absorbent core and a second absorbent core, wherein the first absorbent core and the second absorbent core are disposed offset from one another such that the front end portion comprises only one of the first absorbent core or the second absorbent core and the rear end portion comprises only the other of the first absorbent core or the second absorbent core, wherein a central portion is disposed between the front end portion and the rear end portion; wherein the absorbent system of the first plurality of absorbent articles comprises the central portion having a first length and the absorbent system of the second plurality of absorbent articles comprises the central portion having a second length, wherein the second length is greater than the first length, and wherein the first plurality of absorbent articles comprises a first folded caliper and the second plurality of absorbent articles comprises a second folded caliper, wherein the second caliper is greater than the first caliper.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION

Figure 1:
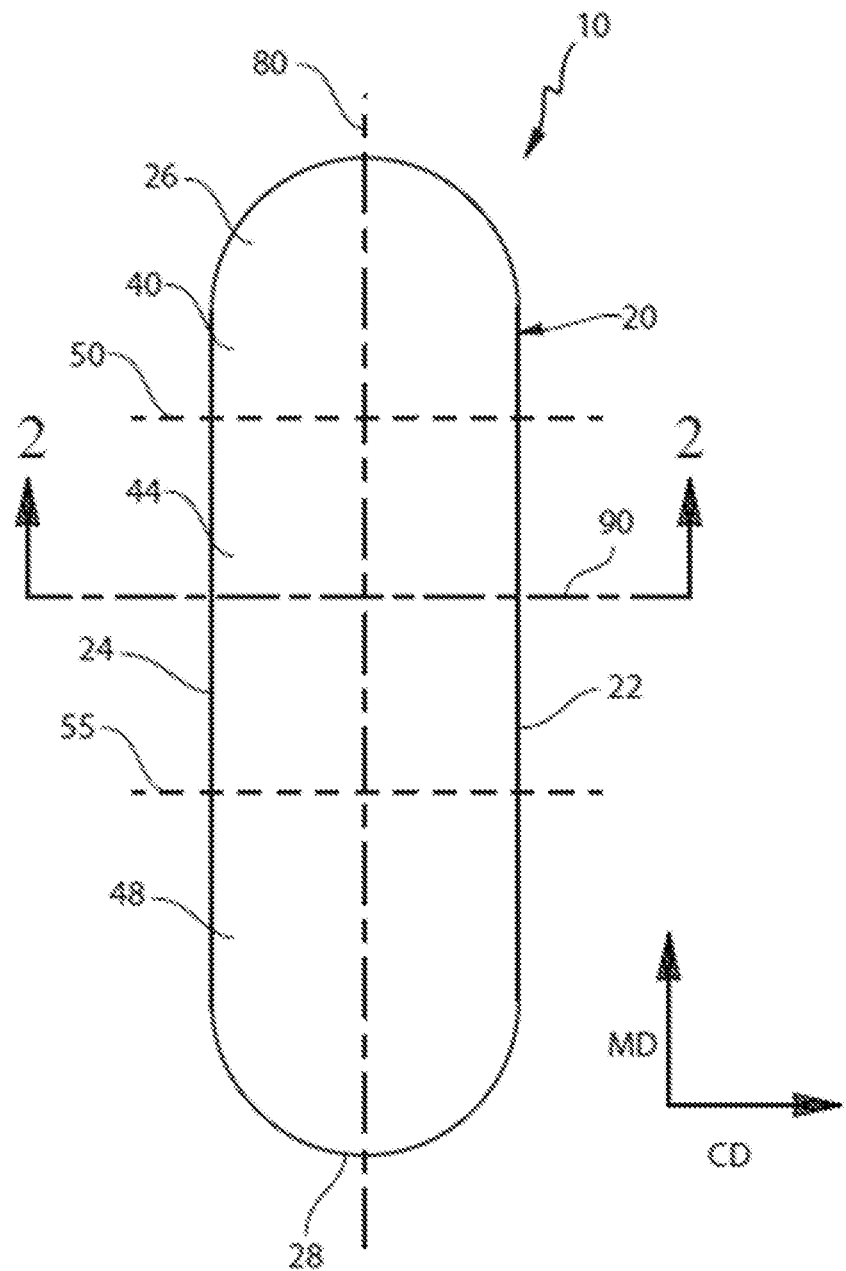
FIG. 1 is a plan view showing an exemplary embodiment of a disposable absorbent article of the present invention, which is an incontinence pad.

The disposable absorbent articles of the present disclosure can provide flexibility to allow for an improved and comfortable fit which is less susceptible to bunching during use. In particular, it is envisioned that the articles of the present disclosure exhibit heightened structural resiliency from the proposed configuration and orientation of the layers contained therein. For the purposes of this disclosure, reference to an incontinence pad, disposable absorbent article, or absorbent article will be used. However, the present invention may be applied to a plurality of absorbent articles including, but not limited to, sanitary napkins, pantiliners, menstrual pads, diapers, training pants, adult incontinence pants, etc.

There are several factors to consider when designing a disposable absorbent article like an incontinence pad, particularly if improved fit and performance are desired. First, the stiffness of the pad is an important factor. Typically, thinner pads offer less stiffness than their bulkier counterparts. Less stiffness can be desirable in some areas of the pad as the lower stiffness areas can allow the pad to conform as needed to the contours of a wearer; however, if not properly managed, then the absorbent article may offer no structural resistance to bunching/compression during wear which can lead to leakage. In contrast, while bulkier pads may be less likely to succumb to the compression that is typical during wear, bulkier pads are less desirable because they can cause the incontinence pad to lose its discreetness during use. Additionally, despite resisting compressive forces during use, bulkier pads are not able to conform as easily as their thinner pad counterparts. This lack of conformance can similarly lead to leakage problems during use.

Second, is the absorbent capacity of the absorbent article. Ideally, the pad is well suited to accommodate either small or large loads of exudates. This accommodation means not only storing either type of load sufficiently but also effectively and quickly wicking such loads from a body-contacting surface of the pad such that the user experiences little to no feeling of wetness after the release of the load. In the case of a small load, a wearer should be able to continue to wear the pad for some reasonable time after a release since immediate changing of the pad may not be feasible or desired.

In the past, conventional incontinence pad designs have required a bit of compromise relative to these factors. In contrast, the absorbent articles designed pursuant to the present disclosure account for these factors to arrive at an absorbent article which exhibits improved protection against leakage, particularly for those wearers of a higher than average body mass index (BMI). Namely, absorbent articles of the present disclosure provide good core flexibility, excellent wicking, distribution, and overall absorbency, and in certain forms, may include barrier cuffs which stand up during use and contact the wearer in an appropriate location are included as part of the construction to further protect against a likelihood of leakage. For the purposes of this disclosure, reference to an incontinence pad, disposable absorbent article, or absorbent article will be used; however, the present disclosure may be applied to a plurality of absorbent articles including, but not limited to, sanitary napkins, pantiliners, menstrual pads, diapers, training pants, adult incontinence pants, etc.

FIG. 1 shows an absorbent article 10 of the present disclosure. The absorbent article 10 comprises a longitudinal axis 80 and a lateral axis 90. The longitudinal axis 80 generally extends parallel to the longest dimension of the absorbent article 10. The lateral axis 90 extends generally perpendicular to the longitudinal axis 80 and lies in the same plane as the absorbent article 10 in a flattened state on a flat surface. The lateral axis 90 bisects the length of the absorbent article 10 where the length is parallel to the longitudinal axis 80, and the longitudinal axis 80 bisects the width of the absorbent article 10 where the width is parallel to the lateral axis 90. Additionally, as shown, the MD direction may be generally parallel to the longitudinal axis 80 of the incontinence pad 10, and the CD direction may be generally parallel to the lateral axis 90.

The absorbent article 10 comprises a generally elongated oval shape. However, any suitable shape may be utilized. Some examples include hourglass (peanut), offset hourglass (one end is wider than an opposite end and a narrowed mid-section between the ends), etc. The incontinence pad 10 may be symmetric about the longitudinal axis 80 or asymmetric about the longitudinal axis 80. Similarly, the absorbent article 10 may be symmetric about the lateral axis 90 or asymmetric about the lateral axis 90.

The absorbent article 10 may further comprise a chassis 20 comprising a plurality of side edges 22 and 24 which extend generally parallel to the longitudinal axis 80. A pair of end edges 26 and 28 join each of the side edges 22 and 24. One end edge 26 joins the side edges 22 and 24 in a first end region 40 of the absorbent article 10 while the other end edge 28 joins the side edges 22 and 24 in a second end region 48 of the absorbent article 10—the second end region 48 being opposite the first end region 40. An intermediate region 44 is disposed between the first end region 40 and the second end region 48.

Figure 2:
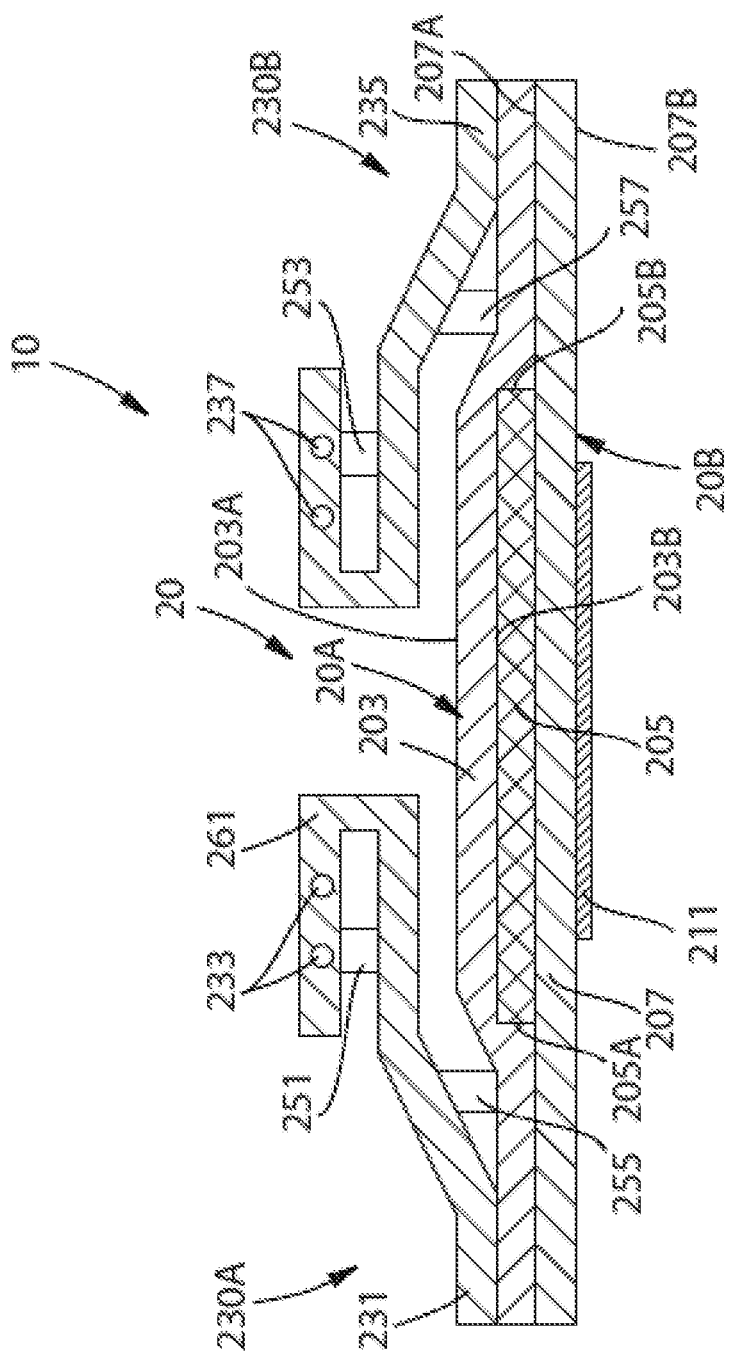
FIG. 2 is a cross-sectional view of the incontinence pad shown in FIG. 1 taken along 2-2.

The chassis 20 of FIG. 1 is shown in cross-section in FIG. 2. Among other things, the chassis 20 comprises a primary topsheet 203. This primary topsheet has a body-facing surface 203A and a garment-facing surface 203B. This chassis 20 of the absorbent article 10 further comprises a backsheet 207 which also comprises its own body-facing surface 207A and opposing garment-facing surface 207B. These two components sandwich an absorbent system 205. In other words, the absorbent system 205 is disposed between the topsheet 203 and the backsheet 207. All three components (i.e., topsheet 203, backsheet 207, and absorbent system 205) form the chassis 20 of the pad 10. Additional layers may very well be included within this chassis 20, particularly between the topsheet 203 and the backsheet 207 but it should be noted that these layers are separate and apart from the absorbent system. Suitable additional layers may include secondary topsheets, acquisition layers, additional distribution layers over and above those which will be discussed below, and other useful layers. In the case of a secondary topsheet, it is disposed beneath the primary topsheet 203 and on the body-facing surface of the core. In certain embodiments, the secondary topsheet (also known as the "STS") has a greater length and width than the absorbent core 205.

The chassis 20 further comprises a wearer-facing surface 20A and a garment-facing surface 20B. The wearer-facing surface 20A may comprise the topsheet 203, and the garment-facing surface 20B may comprise the backsheet.

Figure 3:
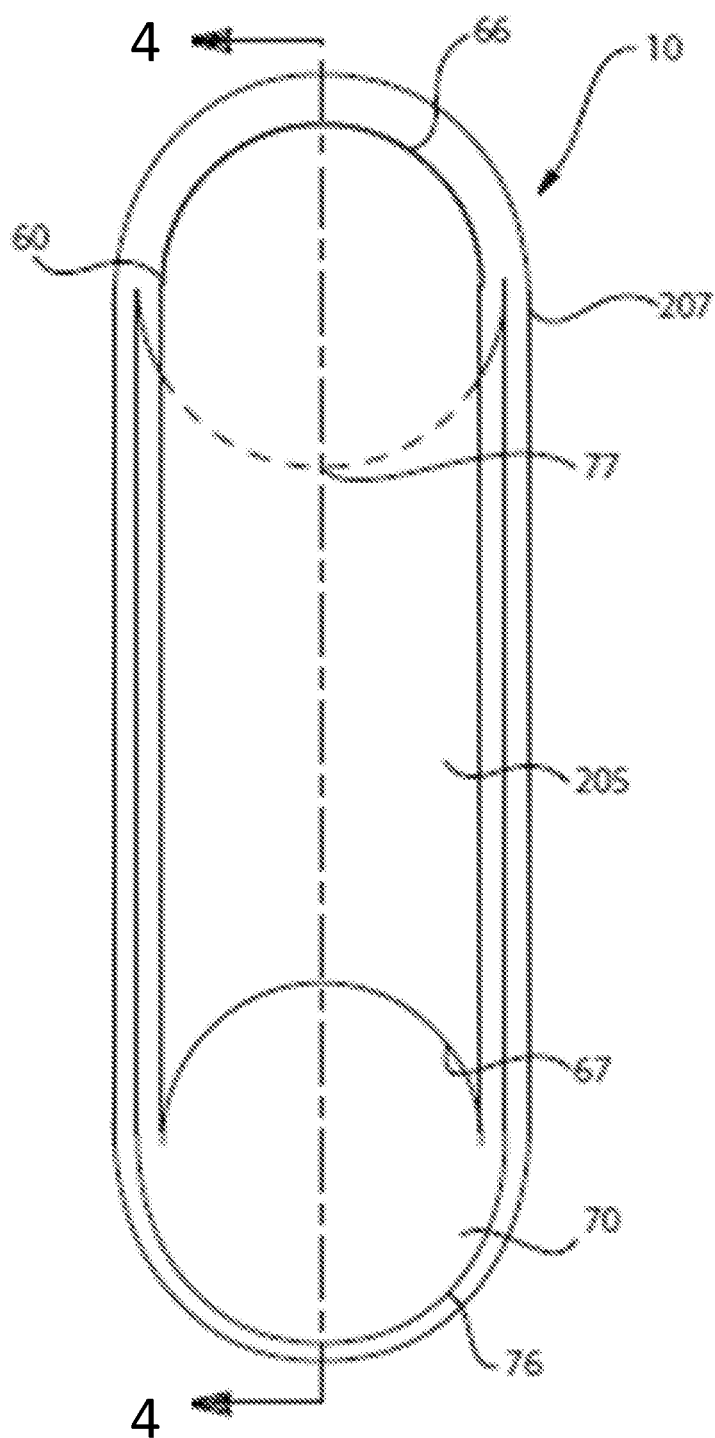
FIG. 3 is a plan view of the pad of FIG. 1 with the primary topsheet removed.
Figure 4A:
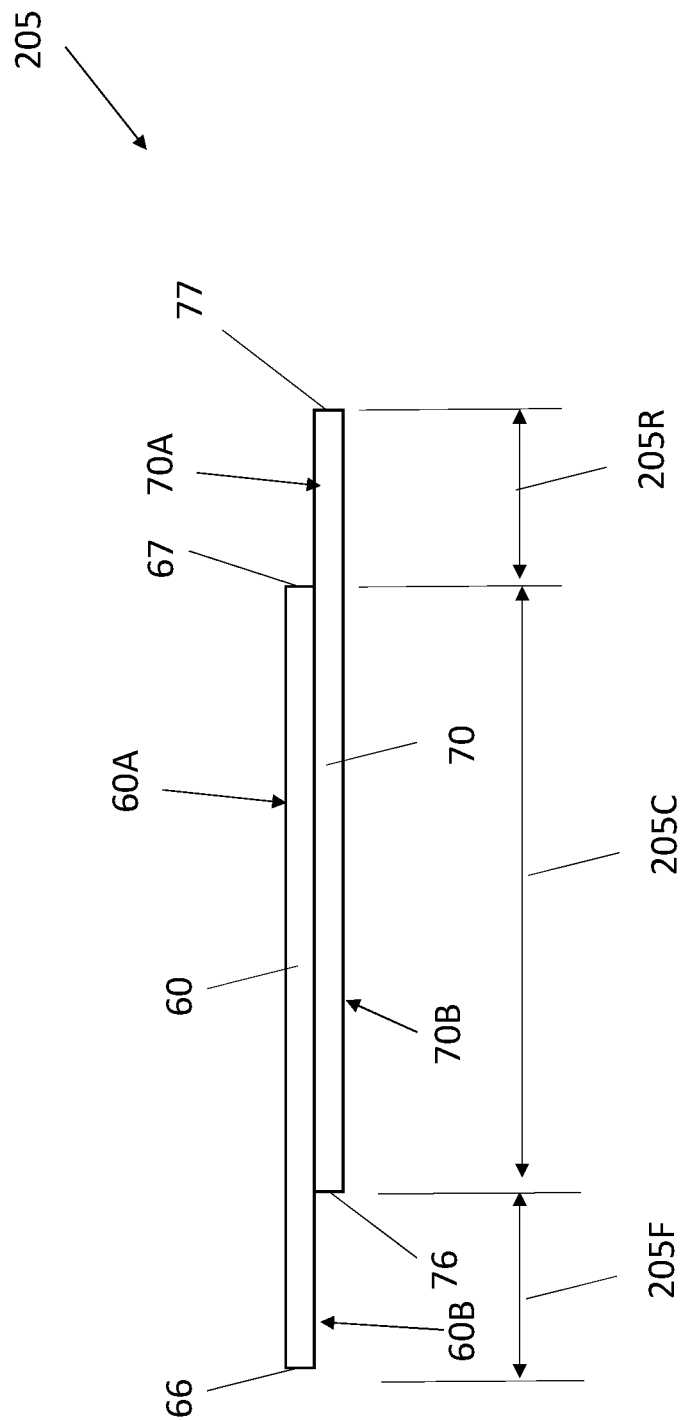
FIG. 4A is a cross-sectional view of the absorbent system of the pad of FIG. 3 taken along 3-3.
Figure 4B:
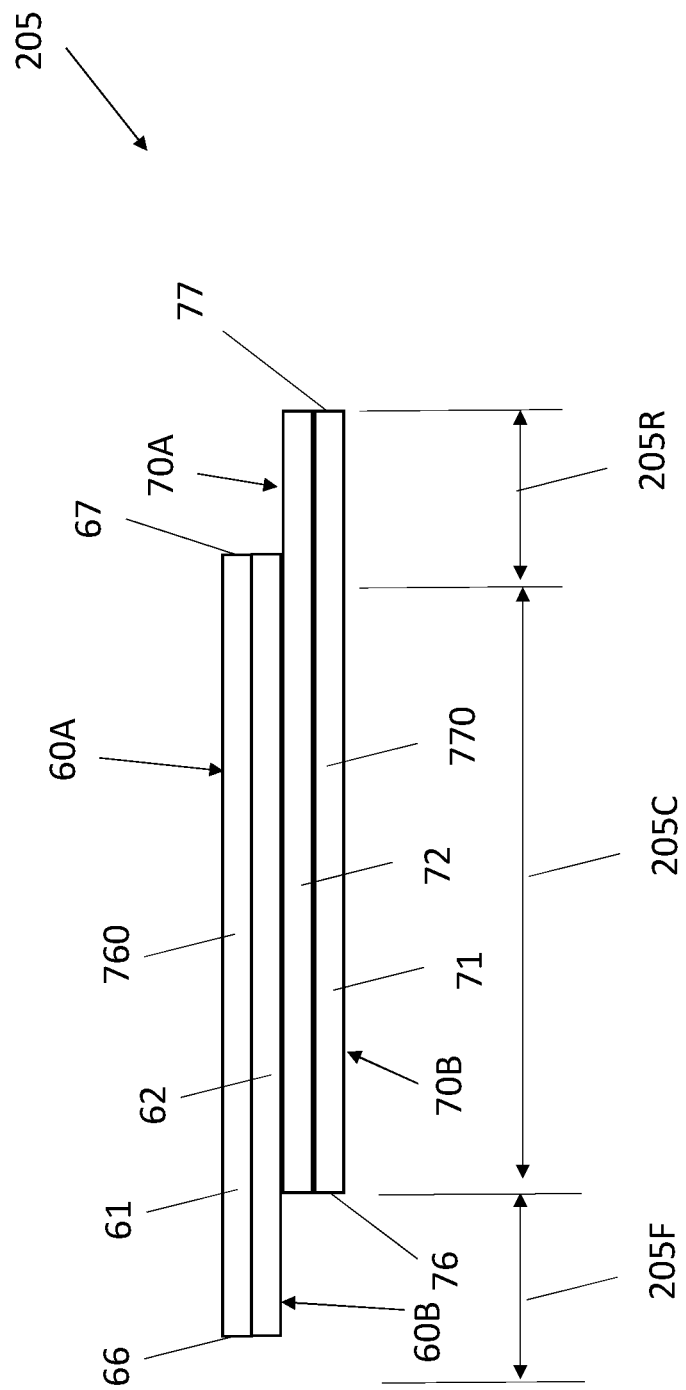
FIG. 4B is a cross-sectional view of another absorbent system that can be utilized in the absorbent articles of the present disclosure.

The absorbent system 205 is formed from multiple layers and is directed to quickly acquiring the bodily fluid or exudates and distributing them along a length of the core. FIGS. 3-4B depict absorbent systems 205 suitable for use with the absorbent articles of the present disclosure. FIG. 3 shows a plan view of the absorbent article 10 with the primary topsheet 203 removed for viewing of the absorbent system 205 positioned above the backsheet 207. The absorbent system 205 comprises a first absorbent core 60 and a second absorbent core 70. As shown, in some forms, the first absorbent core 60 and/or the second absorbent core 70 may comprise laminate structures which include a plurality of layers—see FIG. 4B. Or, in some forms, the first absorbent core 60 and/or the second absorbent core 70 may comprise a single layer of absorbent material—see FIG. 4A.

For those forms where the first absorbent core 60 and/or the second absorbent core comprise a laminate structure any suitable number of layers may be provided in each of these absorbent cores. In some forms, the first absorbent core 60 may comprise a first superabsorbent layer 61 disposed on a first distribution layer 62. The first absorbent core 60 has an upper surface 60A and a lower surface 60B which opposes the upper surface. Additionally, the first absorbent core 60 has a first end 66 and a second end 67 which opposes the first end 66. The absorbent system 205 further includes a second absorbent core 70 which includes a second superabsorbent layer 71 disposed on a second distribution layer 72. This second absorbent core 70 also has an upper surface 70A and a lower surface 70B, a first end 76, and a similar opposing second end 77. As shown, the first distribution layer 62 is joined to the second distribution layer 72 in an offset manner or configuration along the length of the core.

As used herein "offset" or "offset manner" means that the layers or laminates of interest are staggered and that their respective first ends or second ends are not aligned in the z-direction (i.e., the first end of one layer or laminate is not coterminous with the second end of an adjacent underlying or overlying layer or laminate) when the layers or laminates overlay one another. This offset joinder of the first and second distribution layers 62, 72 results in an overlapping and joined area of the two laminates that forms a central portion 205C of the absorbent core 205. The central portion 205C of the core is consequently bounded on each side by a front end portion and a rear end portion 205R, both of the core. In other words, the front end portion 205F and the rear end 205R portion are respectively disposed at opposing ends of the core 205. The front end portion 205F is formed from a first end 66 or second end 67 of the first laminate 60 while the rear end portion 205F of the core 205 is formed by the first end 76 or second end 77 of the second laminate 70. In the form of FIG. 3, the first ends 66, 76 of the first and second laminates oppose each other and form a front end portion 205F and a rear end portion 205R of the absorbent core 205, respectively. In an alternate embodiment, the second ends 67, 77 of the first and second laminates may oppose each other and form a front end portion 205F and a rear end portion 205R of the absorbent core 205, respectively. In both instances, the first ends 66, 76 are in the form of a male connection derived from a nested cut of the first and second laminates. Similarly, the second ends 67, 77 are in the form of a female connection derived from a nested cut of the first and second laminates, respectively. The form of FIG. 4A may be similarly configured as the absorbent system 205 of FIG. 4B.

The front end portion 205F comprises a front end length, and the rear end portion 205R comprise a rear end length. In some forms, the front end length may be equal to the rear end length. Forms are contemplated where the front end length and the rear end length are different. For example, the front end length may be greater than the rear end length. As another example the rear end length may be greater than the front end length.

The length of the central portion 205C can vary by size of the absorbent article 10. For example, for those absorbent articles sized for higher BMI wearers, the length of the central portion 205C can be higher than the central portion 205C for absorbent articles sized for wearers having a lower BMI. Additionally, where the absorbent articles are equipped with elasticated barrier leg cuffs, the central portion 205C may extend past the outermost anchor points of the elastomeric members of the barrier leg cuffs. Extension of the central portion 205C past the outermost anchor points can reduce the likelihood of the ends of the absorbent article folding during application of the absorbent article. Folding ends during application of the absorbent article can be problematic as described in U.S. Patent Application No. 2017/0049634. In some forms, the central portion 205C may have a length of at least 50 mm, at least 75 mm, at least 90 mm, at least 100 mm, at least 125 mm, at least 150 mm, at least 175 mm, at least 200 mm, at least 225 mm, at least 250 mm, 275 mm, 300 mm, 325 mm, 350 mm, or 375 mm, specifically including all values within these ranges and any ranges created thereby.

In some forms, the first absorbent core 60 and the second absorbent core 70 may be joined to one another in a slightly different configuration with the first distribution layer 62 joined to the second superabsorbent layer 71 instead of the second distribution layer. In this instance, the laminates are joined to one another in an offset manner as well except the first distribution layer 62 is joined to the second superabsorbent layer 71 instead of the second distribution layer. The form of FIG. 4A may be similarly configured to the absorbent system of FIG. 4B.

Still in other forms, the first absorbent core 60 is joined to the second absorbent core 70 by whichever superabsorbent layer or distribution layer of the other that is most suitable for the purpose of the resultant article. This joinder is also done in an offset manner that results in a lengthier core with a thicker central portion than the front and rear portions.

In some forms, the overlapping area or region that forms the central portion 205C of the core 205 has at least one characteristic of a greater capacity, a greater void volume, or a greater thickness than the front end portion 205F and the rear end portion 205F of the absorbent core 205. This embodiment is particularly useful for providing for heightened leakage protection in the central portion where female users of such pads would typically contact the pad and release fluids.

Fold Lines

Referring back to FIG. 1, absorbent article 10 may further comprise a first fold line 50 and a second fold line 55. The first fold line 50 can define a boundary between the first end region 40 and the intermediate region 44. The second fold line 55 can define a boundary between the second end region 48 and the intermediate region 44. The first end region 40 can be defined by the end edge 26, the first fold line 50, and a portion of the side edges 22 and 24 disposed between the end edge 26 and the first fold line 50. The intermediate area 44 can be defined by the first fold line 50, the second fold line 55, and a portion of the side edges 22 and 24 disposed between the first fold line 50 and second fold line 55. The second end region 48 is defined by the second fold line 55, end edge 28, and a portion of the side edges 22 and 24 disposed between the end edge 28 and the second fold line 55. The fold lines 50 and 55 can be parallel and can be co-linear (on average) with the folds which are created via the packaging process for the incontinence pad 10.

In some forms, the first fold line 50 and second fold line 55, may be configured such that the fold lines 50 and 55 dissect the pad into thirds. In other forms, the first fold line 50 may be offset toward the end edge 28, and the second fold line 55 may be offset toward the end edge 28. In such forms, this can allow the second end region 48 to be tucked between the intermediate region 44 and the first end region 40 when the pad is in the folded configuration.

The inventors have found that the placement of the fold lines can impact the absorbent article 10 in a variety of ways. For example, folds which are placed too far inboard from elastomeric anchor points, as described in U.S. Patent Application Publication No. 2017/0049634, can lead to problems during application of the article to a user's underwear. Additionally, for the absorbent articles of the present disclosure, the placement of the folds can impact the caliper of the folded article. This caliper can in turn impact the discreetness of the folded article as thicker articles may generally be perceived as non-discreet or less discreet than their thinner counterparts. This can particularly be the case where light absorbency products are desired/utilized. Some consumers may however, perceive thinner more discreet articles as offering less protection than their thicker counterparts. This can particularly be the case where higher absorbency products are desired/utilized.

This may be particularly problematic where different absorbency levels of absorbent articles have the same overall length and/or width. In such forms, the differing absorbency levels may be achieved via higher basis weights of superabsorbent, higher basis weights of cellulose, etc. Unfortunately, such changes may not be very noticeable to the wearer. For example, an increase in the basis weight of superabsorbent by 10 gsm or 20 gsm which can provide a consumer noticeable increase in absorbency, may only yield small change in caliper of the folded absorbent article. So, upon comparison of the two articles by a wearer, the wearer may feel like any claims of increased absorbency to be inaccurate.

Figure 5A:
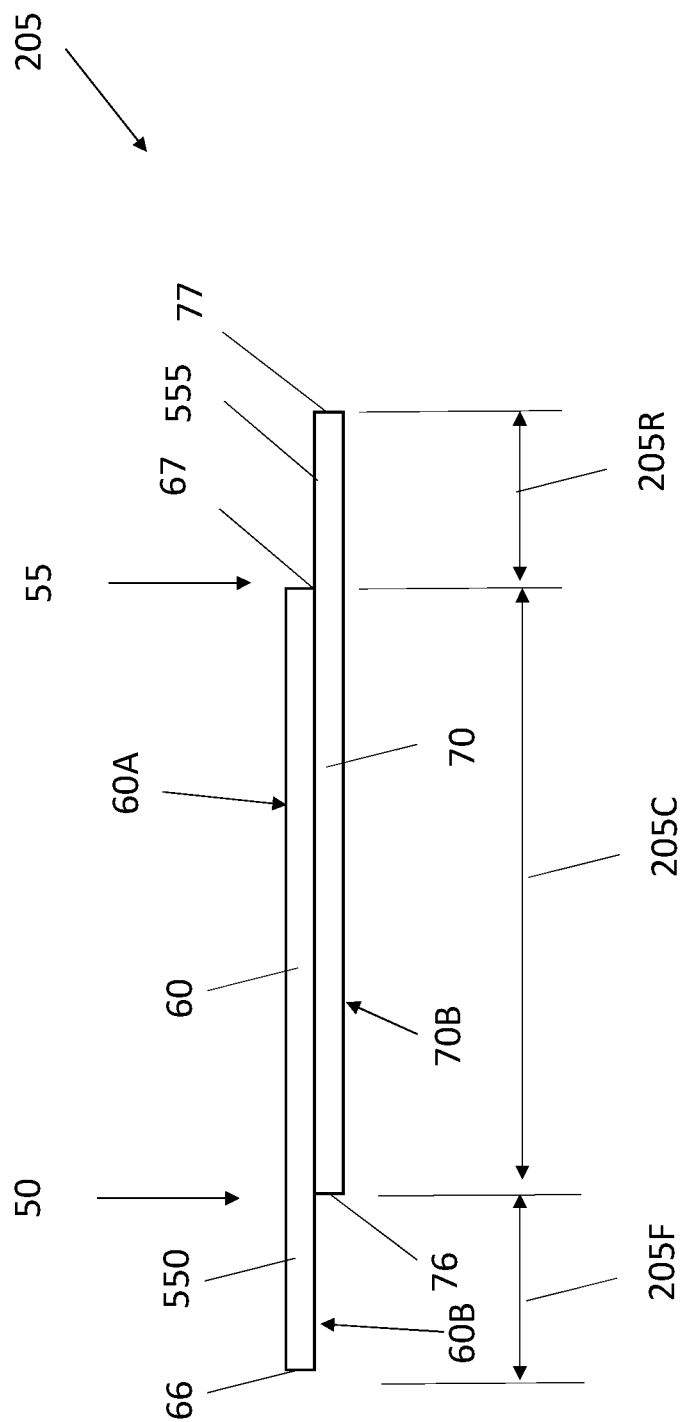
FIG. 5A is a cross-sectional view of the absorbent system of FIG. 4A with a first fold line and a second fold line indicated.
Figure 5B:
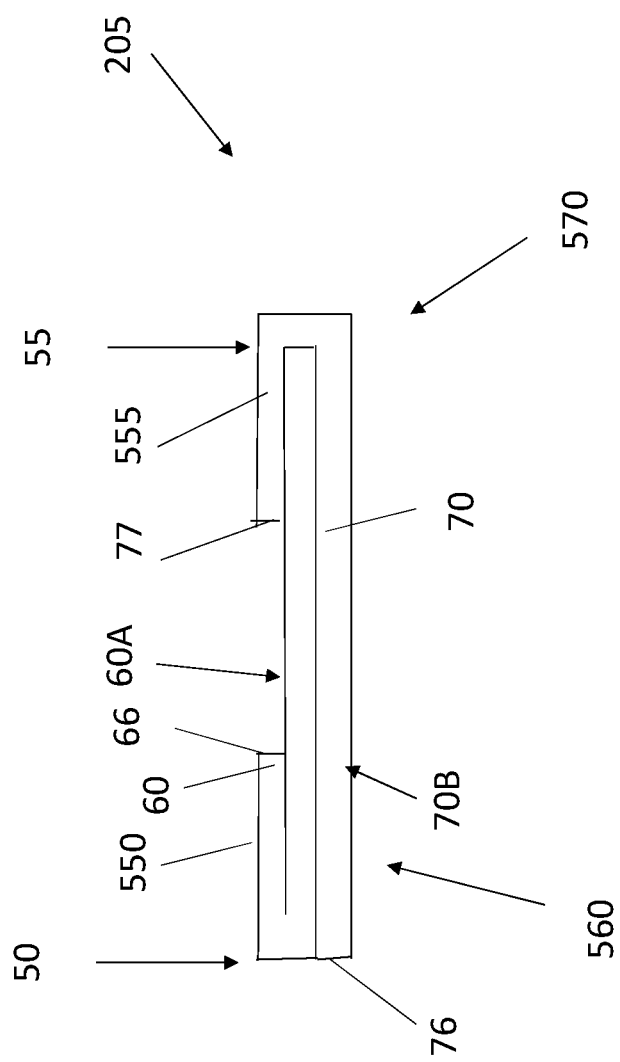
FIG. 5B is a cross-sectional view of the absorbent system of FIG. 5A in a tri-folded configuration.

Referring to FIGS. 5A and 5B, forms are contemplated where first fold line 50 is created in the front end portion 205F of the absorbent system, and the second fold line 55 is created in the rear end portion 205R of the absorbent system. A first fold portion 550, comprising the first end 66 of the first absorbent core 60 is created via the first fold line 50. A second fold portion 555, comprising the second end 77 of the second absorbent core 70 is created via the second fold line 55. For such forms, a thinner overall caliper may be realized post folding of the article. For example, the folded article will only have three layers of the absorbent system 205 which make up its caliper in a first fold area 560. Similarly, where the second fold line 55 is disposed in the rear end portion 205R of the absorbent system, the folded article will only have three layers of the absorbent system 205 in a second fold area 570. For those forms where the first absorbent core 60 and/or the second absorbent core 70 comprise a laminate structure, the above placement of the first fold line 50 and the second fold line 55 also may yield a thinner caliper folded absorbent article.

Table 1 below shows prophetic examples of folded article calipers. The calipers were estimated based upon measured calipers of all components of exemplary absorbent articles of the present disclosure, e.g. topsheet, secondary topsheet, the first absorbent core, the second absorbent core, and backsheet. Each of the first and second absorbent cores comprise laminate structures as depicted in FIG. 4B. Additionally, calipers were estimated based upon varying basis weights of the distribution layers in each of the first absorbent core 60 and the second absorbent core 70.

TABLE 1

| Basis weight of Distribution Layer (gsm) | Unfolded Center Caliper (mm) | Unfolded Caliper at fold line (mm) | Tri-fold caliper no overlapping ends (mm) | Tri-fold caliper with overlapping ends (mm) |
|---|---|---|---|---|
| 120 | 5.7 | 3.3 | 9.0 | 12.3 |
| 135 | 6.1 | 3.5 | 9.6 | 13.1 |
| 150 | 6.5 | 3.7 | 10.2 | 13.9 |
| 160 | 6.7 | 3.8 | 10.5 | 14.4 |

As noted previously, where lighter absorbency products are desired, a more discreet folded article may be preferential by the wearer. As shown in Table 1, where the first fold portion 550 and the second fold portion 555 do not overlap, it is believed that the caliper of a tri-folded article constructed in accordance with the present disclosure can be less than 11 mm, or less than 10 mm, specifically reciting all values within these ranges and any ranges created thereby.

Figure 5C:
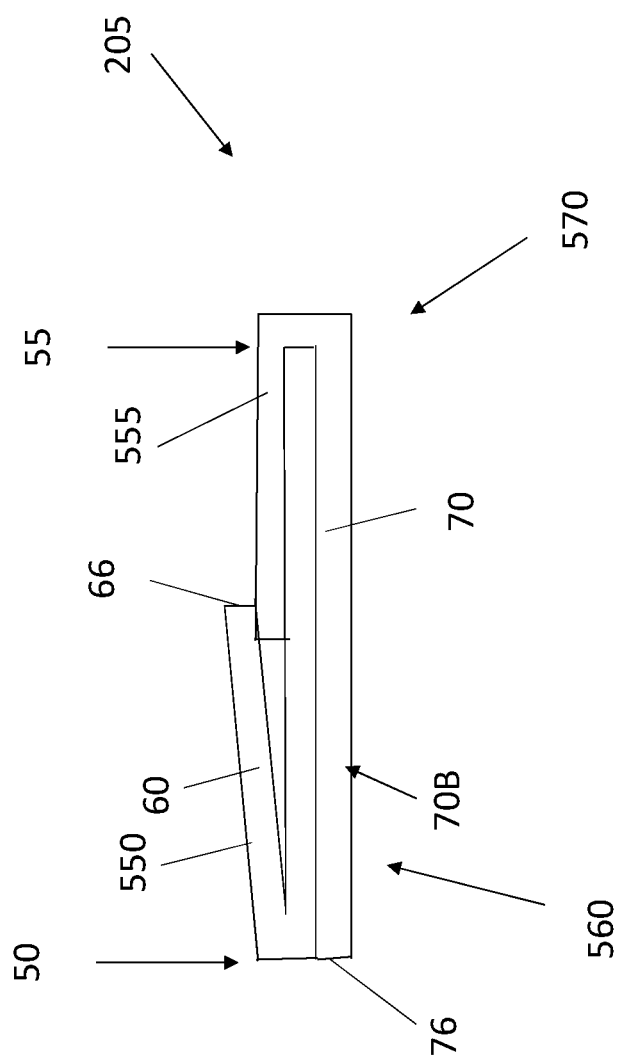
FIG. 5C is a cross-sectional view of the absorbent system of FIG. 5A in another tri-folded configuration.

For those forms where the first fold portion 550 and the second fold portion 555 overlap in the folded state (as shown in FIG. 5C), the caliper of a tri-folded article constructed in accordance with the present disclosure can still yield a relatively thin article. For example, it is believed that the caliper of tri-folded articles constructed in accordance with the present disclosure can have a caliper of less than 15 mm, less than 14 mm, or less than 13 mm, specifically including all values within these ranges and any ranges created thereby.

Figure 6A:
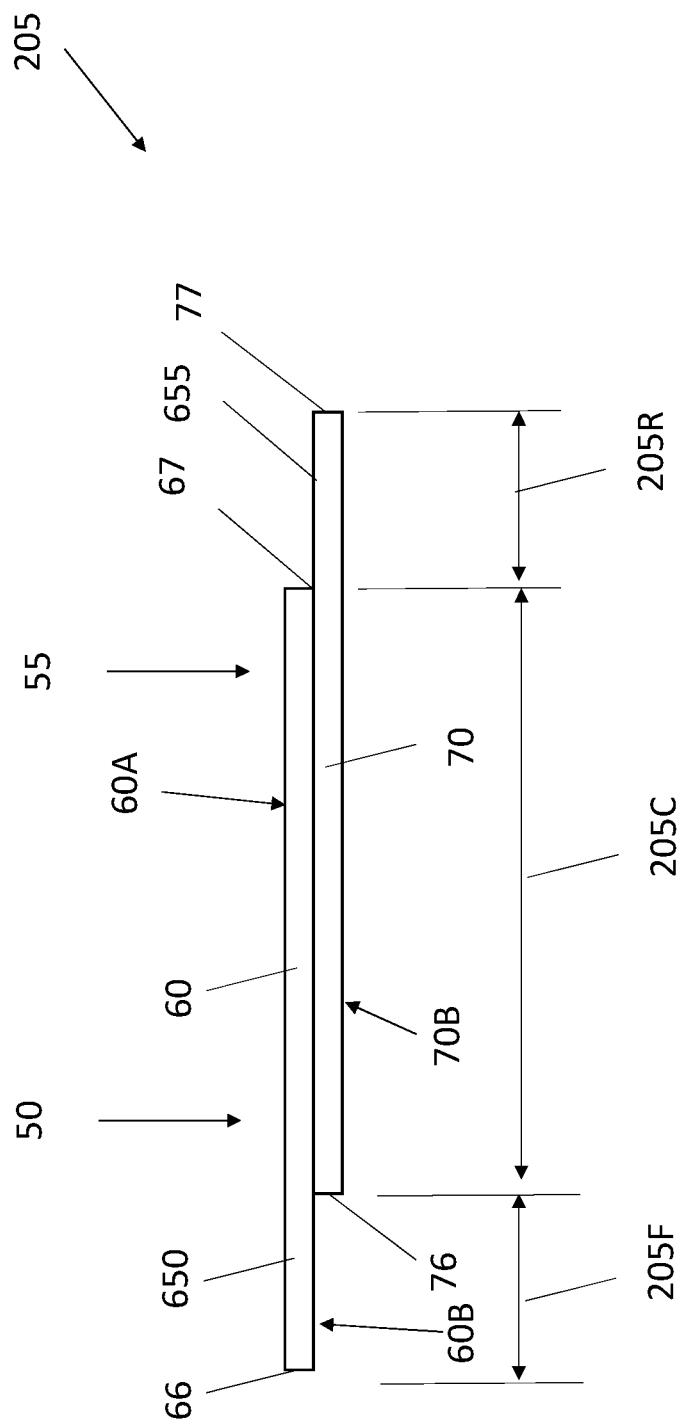
FIG. 6A is a cross-sectional view of the absorbent system of FIG. 4A with another configuration for a first fold line and a second fold line.
Figure 6B:
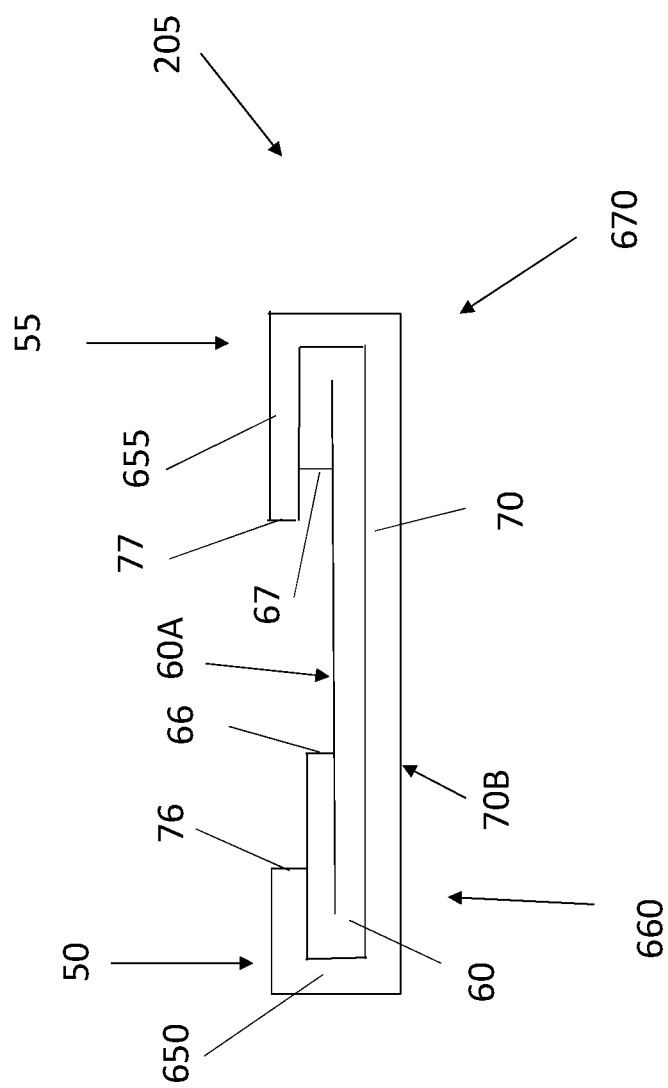
FIG. 6B is a cross-sectional view of the absorbent system of FIG. 6A in a tri-folded configuration.

Referring to FIGS. 6A and 6B, forms are contemplated where first fold line 50 and/or the second fold line 55 is created in the central portion 205C of the absorbent system. A first fold portion 650, comprising the first end 66 of the first absorbent core 60 is created via the first fold line 50. A second fold portion 655, comprising the second end 77 of the second absorbent core 70 is created via the second fold line 55. For such forms, a higher overall caliper may be realized post folding of the article. For example, the folded article will have four layers of the absorbent system 205 which make up its caliper in a first fold area 660. Similarly, where the second fold line 55 is disposed in the rear central portion 205C of the absorbent system, the folded article will have four layers of the absorbent system 205 in a second fold area 670. For those forms where the first absorbent core 60 and/or the second absorbent core 70 comprise a laminate structure, the above placement of the first fold line 50 and the second fold line 55 also may yield a higher caliper folded absorbent article.

Table 2 below shows prophetic examples of folded article calipers. The calipers were estimated based upon measured calipers of the first absorbent core and the second absorbent core. Each of the first and second absorbent cores comprise laminate structures as depicted in FIG. 4B. Additionally, calipers were estimated based upon varying basis weights of the distribution layers in each of the first absorbent core 60 and the second absorbent core 70.

TABLE 2

| Basis weight of Distribution Layer (gsm) | Unfolded Center Caliper (mm) | Unfolded Caliper at fold line (mm) | Tri-fold caliper no overlapping ends (mm) | Tri-fold caliper with overlapping ends (mm) |
|---|---|---|---|---|
| 120 | 5.7 | 5.7 | 11.4 | 17.0 |
| 135 | 6.1 | 6.1 | 12.2 | 18.2 |
| 150 | 6.5 | 6.5 | 13.0 | 19.4 |
| 160 | 6.7 | 6.7 | 13.4 | 20.2 |

As noted previously, where higher absorbency products are desired, a thicker caliper folded article may be preferential by the wearer. As shown in Table 2, where the first fold portion 650 and the second fold portion 655 do not overlap, it is believed that the caliper of a tri-folded article constructed in accordance with the present disclosure can be greater than 10 mm, greater than 12 mm, or greater than 13 mm, specifically reciting all values within these ranges and any ranges created thereby.

Where the fold lines (or at least one of the fold lines) are disposed in central portion 205C of the absorbent system, a ratio of folded article caliper highest absorbency to a lower absorbency (within the same class, i.e. pads v. pads, liners v.

liners, but not pads v. liners) can be from about 2.0 to 1.0, from about 1.8 to 1.0, from about 1.5 to 1.0, from about 1.4 to 1.0, or from about 1.2 to 1.0, specifically reciting all values within these ranges and any ranges created thereby.

Where the fold lines are disposed outboard of the central portion 205C of the absorbent system, a ratio of folded article caliper highest absorbency to a lower absorbency (within the same class, i.e. pads v. pads, liners v. liners, not pads v. liners) can be from about 1.6 to 1, from about 1.4 to about 1.0, from about 1.2 to about 1.0, or from about 1.1 to about 1.0, specifically reciting all values within these ranges and any ranges created thereby.

Additionally, to accommodate the desires of a wide variety of consumers, caliper ratios may be adjusted such that those users wanting a more discreet folded article, e.g. lower caliper, versus those that want to "see" a thicker article for peace of mind, e.g. higher caliper, may be satiated. For example, caliper ratios of folded article caliper highest absorbency to a lower absorbency (within the same class, i.e. pads v. pads) can be between about 2.5 to about 1.0, from about 2.3 to about 1.0, from about 2.0 to about 1.0, or from about 1.6 to about 1.0, specifically including all values within these ranges and any ranges created thereby. Such configurations may be accomplished by providing some absorbent articles with fold lines which are outside the central portion 205C and some articles which have fold lines within the central portion 205C. For example, higher absorbency absorbent articles may have fold lines within the central portion 205C whereas lower absorbency absorbent articles may have fold lines which are outside of the central portion 205C.

The indication of higher absorbency or lower absorbency absorbent articles is typically provided on the absorbent article packaging. For example, some packages may show/highlight 5 drops of liquid for their highest absorbency offering, while a lower absorbency offering may show/highlight 4 drops of liquid or less. Or, some may utilize a numbering system where 5 is their highest absorbency offering and 1 is their lowest. It is expected that one of ordinary skill in the art, when looking at an absorbent article package, would be able to determine a higher/highest absorbency absorbent article package from a lower/lowest absorbency absorbent article package.

For those forms where the first fold portion 650 and the second fold portion 655 overlap in the folded state, the caliper of a tri-folded article constructed in accordance with the present disclosure can still yield a relatively thin article. For example, it is believed that the caliper of tri-folded articles constructed in accordance with the present disclosure can have a caliper of greater than 15 mm, greater than 16 mm, greater than 17 mm, or greater than 19 mm, specifically including all values within these ranges and any ranges created thereby.

Forms are contemplated where the first edge 66 of the first absorbent core 60 overlaps the second edge 77 of the second absorbent core 70. In such forms, caliper of the folded absorbent article may be increased versus that of the configuration shown in FIG. 6B. Forms are contemplated where the first edge 66 overlaps the second edge 67 of the first absorbent core. In such forms, the first edge 76 of the second absorbent core 70 and the second edge 77 of the second absorbent core 70 may similarly overlap. However, this is not necessarily the case. In such forms, the first folded area 660 or the second folded area 670 may comprise five layers of the absorbent system 205. Additional forms are contemplated from such forms where the first edge 76 and the second edge 77 of the second absorbent core 70 overlap. In such forms, the first folded portion 660 or the second folded area may comprise six layers of the absorbent system 205. Of course, where the first absorbent core 60 and the second absorbent core 70 comprise laminate structures, additional layers may be comprised by the first folded area 660 and/or the second folded area 670.

As discussed previously, depending on the placement of the fold lines, the caliper of the folded article may be greatly impacted. Folded absorbent articles have a folded length and a folded width in addition to their folded caliper. For wearer's with higher BMI's, absorbent articles generally increase in length and width which in turn can impact their folded length and width. For example, the folded length (generally parallel to the longitudinal centerline of the article) can range from about 60 mm to about 160 mm, or from about 70 mm to about 150 mm, specifically including all values within these ranges and any ranges created thereby. The ends of the above ranges may represent the smallest sizes and the largest sizes where intermediate sizes comprise values within these ranges. For example, intermediate sizes may comprise a folded length of about 90 mm, 100 mm, 120 mm, 130 mm, and/or 140 mm.

The folded width (generally parallel to the transverse centerline of the absorbent article) can range from about 70 mm to about 140 mm, or from about 80 mm to about 120 mm, specifically including all values within these ranges and any ranges created thereby. The ends of the above ranges may represent the smallest sizes and the largest sizes where intermediate sizes comprise values within these ranges. For example, intermediate sizes may comprise a folded width of about 90 mm, 100 mm, 105 mm, 110 mm, and/or 120 mm.

Forms are contemplated where an array of products is provided. A first plurality of products within the array may have an overall first length, and a second plurality of products within the array of products may have an overall second length. The first length and the second length may be equal. The second plurality of products may have a higher absorbent capacity than that of the first plurality of products. The higher absorbent capacity may be communicated via packaging for the second plurality of absorbent articles.

The first plurality of products may have a first folded length and a first folded width, and the second plurality of products may have a second folded length and a second folded width. The first folded length may be within plus or minus 10 percent of the second folded length. Similarly, the first folded width may be within plus or minus 10 percent of the second folded width. The folded caliper of the second plurality of absorbent articles may be greater than the folded caliper of the first plurality of absorbent articles. For example, in some forms, the folded caliper may be greater than about 10 percent, greater than about 20 percent, greater than about 30 percent, greater than about 40 percent, greater than about 50 percent, specifically reciting all values within these ranges or any ranges created thereby.

In some forms, each of the first plurality of absorbent articles and each of the second plurality of absorbent articles may comprise an absorbent system as described herein. In such forms, the central portion 205C (shown in FIG. 4A-4B) of each of the second plurality of absorbent articles may have a length which is greater than a length of the central portion 205C of the first plurality of absorbent articles.

In some forms, an array of absorbent articles may comprise a first plurality of absorbent articles, a second plurality of absorbent articles, and a third plurality of absorbent articles. Each of the first, second, and third plurality of absorbent articles may comprise the absorbent system 205 as described herein. For example, each of the first, second, and third pluralities of absorbent articles may comprise a first absorbent core and a second absorbent core disposed in an offset manner with respect to one another. Each of the first plurality, second plurality, and third plurality of absorbent articles may comprise differing lengths and differing levels of absorbency. Additionally, at least two of the first plurality, second plurality, and/or third plurality may comprise differing basis weights of superabsorbent layers, distribution layers, and/or of absorbent cores. Each of the first plurality of absorbent articles, second plurality of absorbent articles, and third plurality of absorbent articles may comprise a folded caliper, wherein the folded caliper increases with increasing absorbent capacity. In some forms, the first plurality of absorbent articles, second plurality of absorbent articles, and third plurality of absorbent articles may comprise a folded length and a folded width. In some forms, the folded length and/or folded width may increase with increasing absorbent capacity. In some forms, the central portion 205C may a comprise a length, wherein the length of the central portion 205C increases with increasing absorbent capacity.

Applicant shall now provide more detailed insight into the individual components of the disposable absorbent articles envisioned herein.

Primary Topsheet

Referring back to FIGS. 3-4, the primary topsheet 203 (also referred to herein "topsheet") of the chassis 20 is positioned adjacent a body-facing surface 203A of the absorbent system 205 and may be joined thereto and to the backsheet 207 by attachment methods (not shown) such as those well known in the art. Suitable attachment methods are described with respect to joining the backsheet 207 to the absorbent system 205. The topsheet 203 and the backsheet 207 may be joined directly to each other in the incontinence pad periphery and may be indirectly joined together by directly joining them to the absorbent system 205 or additional optional layers within the chassis like a secondary topsheet which spans the entire or partial area of the article. This indirect or direct joining may be accomplished by attachment methods which are well known in the art.

The absorbent article may comprise any known or otherwise effective primary topsheet, such as one which is compliant, soft feeling, and non-irritating to the wearer's skin. Suitable primary topsheet materials include a liquid pervious material that is oriented towards and contacts the body of the wearer permitting bodily discharges to rapidly penetrate through it without allowing fluid to flow back through the topsheet to the skin of the wearer. The primary topsheet, while being capable of allowing rapid transfer of fluid through it, also provides for the transfer or migration of the lotion composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof. Some suitable examples of films that can be utilized as topsheets are described in U.S. Pat. Nos. 3,929,135; 4,324,246; 4,342,314; 4,463,045; 5,006,394; 4,609,518; and 4,629,643.

Nonlimiting examples of woven and nonwoven materials suitable for use as the topsheet include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452.

In some forms, the topsheet may comprise tufts as described in U.S. Pat. Nos. 8,728,049; 7,553,532; 7,172,801; 8,440,286; 7,648,752; and 7,410,683. The primary topsheet may have a pattern of discrete hair-like fibrils as described in U.S. Pat. No. 7,655,176 or 7,402,723. Additional examples of suitable topsheet includes those described in U.S. Pat. Nos. 8,614,365; 8,704,036; 6,025,535 and in U.S. Patent Application Publication Nos 13743M.

Another suitable primary topsheet or a primary topsheet combined with a secondary topsheet may be formed from a three-dimensional substrate as detailed in a U.S. Patent Application Publication No. 2017/0258647 A1.

The primary topsheet may have one or more layers, as described in U.S. Patent Application Publication Nos. 2016/0167334 A1; 2016/0166443 A1; 2017/0258651 A1. The topsheet may be apertured as disclosed in U.S. Pat. No. 5,628,097, to Benson et al., issued on May 13, 1997.

Secondary Topsheet

As noted previously, the disposable absorbent articles of the present disclosure may comprise additional layers, one of which includes a secondary topsheet. As mentioned previously, the secondary topsheet may be separate and apart from the absorbent system. Additionally, the secondary topsheet is disposed beneath the primary topsheet 203 and on the body-facing surface of the core. In some forms, the secondary topsheet may have a basis weight from about 40 gsm to about 100 gsm, from about 45 gsm to about 75 gsm, or from about 50 gsm to about 60 gsm, specifically including all values within these ranges and any ranges created thereby. In some forms, the secondary topsheet may comprise a homogeneous mix of fibers.

Some exemplary secondary topsheets are described in U.S. Patent Application Publication Nos. 2015/0351976 A1 and 2014/0343523 A1; and U.S. patent application Ser. No. 15/729,704. Forms are contemplated where the carrier web comprises a secondary topsheet.

Backsheet

The backsheet 207 of the chassis 20 may be positioned adjacent a garment-facing surface of the absorbent system 205 and may be joined thereto by attachment methods (not shown) such as those well known in the art. For example, the backsheet 207 may be secured to the absorbent system 205 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent system 205 is not joined to the backsheet 207, the topsheet 203, or both.

The backsheet 207 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent system 205 from wetting articles of clothing which contact the incontinence pad 10 such as undergarments. However, in some instances, the backsheet 207 may permit vapors to escape from the absorbent system 205 (i.e., is breathable) while in other instances the backsheet 207 may not permit vapors to escape (i.e., non-breathable). Thus, the backsheet 205 may comprise a polymeric film such as thermoplastic films of polyethylene or polypropylene. A suitable material for the backsheet 207 is a thermoplastic film having a thickness of from about 0.012 mm (0.5 mil) to about 0.051 mm (2.0 mils), for example. Any suitable backsheet known in the art may be utilized with the present invention.

Some suitable examples of backsheets are described in U.S. Pat. Nos. 5,885,265; 4,342,314; and 4,463,045. Suitable single layer breathable backsheets for use herein include those described for example in GB A 2184 389, GB A 2184 390, GB A 2184 391, U.S. Pat. Nos. 4,591,523, 3,989,867, 3,156,242; WO 97/24097 and U.S. Pat. Nos. 6,623,464; 6,664,439 and 6,436,508.

The backsheet may have two layers: a first layer comprising a gas permeable aperture formed film layer and a second layer comprising a breathable microporous film layer as described in U.S. Pat. No. 6,462,251. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Absorbent System

The absorbent system 205 of the present invention may comprise any suitable shape. As noted previously, as the absorbent system 205 is typically the stiffest portion of the absorbent article. So, shapes which are useful for the articles of the present disclosure, will typically comprise a reduced width intermediate region. For example, in some forms of the present invention, the absorbent system 205 may comprise a contoured shape, e.g. narrower in the intermediate region than in the end regions. As yet another example, the absorbent system may comprise a tapered shape having a wider portion in one end region of the pad which tapers to a narrower intermediate and end region in the other end region of the pad. The absorbent system 205 may comprise varying stiffness in the MD and CD.

As detailed earlier, the absorbent system 205 comprises the first absorbent core and the second absorbent core. And as described herein the first absorbent core and/or the second absorbent core may comprise a single layer or multiple layers. Both are generally compressible, conformable, non-irritating to the wearer's skin, and capable of absorbing and retaining liquids such as urine and other certain body exudates including menses.

The configuration and construction of the absorbent system 205 may vary (e.g., the absorbent system 205 may have varying caliper zones, a hydrophilic gradient, a superabsorbent gradient, or lower average density and lower average basis weight acquisition zones). Further, the size and absorbent capacity of the absorbent system 205 may also be varied to accommodate a variety of wearers. However, the total absorbent capacity of the absorbent system 205 should be compatible with the design loading and the intended use of the disposable absorbent article or incontinence pad 10.

In some forms of the present disclosure, the absorbent system 205 may comprise a plurality of multi-functional layers that are in addition to the first and second absorbent cores. For example, the absorbent system 205 may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself.

The absorbent system 205 of the present disclosure may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066; WO 95/11652; U.S. Pat. Publ. No. 2008/0312622A1; and WO 2012/052172. These may be used to configure the superabsorbent layers.

Additions to the core of the present disclosure are envisioned. In particular, potential additions to the current multi-laminate absorbent core are described in U.S. Pat. Nos. 4,610,678; 4,673,402; 4,888,231; 4,834,735; 5,234,423; and 5,147,345. These are useful to the extent they do not negate or conflict with the effects of the below described layers of the absorbent core of the present invention.

The first and second absorbent cores layers and/or laminates of the absorbent system 205 have been detailed earlier but it is important to note that these layers or laminates may have cross-direction widths that are the same as each other or different. As discussed previously, for example, the first absorbent core layer or laminate may have a lesser cross-direction width than said second absorbent core layer or laminate or a greater cross-direction width than said second absorbent core layer or laminate. In certain instances, the first and second absorbent core layers or laminates can have machine-direction lengths that are the same while in other instances, the first and second absorbent cores have machine-direction lengths that are different. In the latter instance, the first absorbent core layer or laminate may have a lesser machine-direction length than the second absorbent core layer or laminate, or conversely the first absorbent core layer or laminate may have a greater machine-direction length than said second absorbent core layer or laminate.

The first and second absorbent core layers or laminates in some forms, may further comprise an optional intermediate layer disposed between the respective superabsorbent layer and distribution layer. This optional intermediate layer may comprise materials detailed herein relative to the optional layers for the chassis, in general.

Additionally, in some forms, in addition to the first and second absorbent cores layers or laminates, the absorbent article or incontinence pad may further comprise an optional additional absorbent core comprising a superabsorbent layer and/or a distribution layer. This optional additional core may take the form of a third, fourth, fifth, or even additional layers. The superabsorbent layer and distribution layer may exhibit the same or different properties detailed earlier with respect to the first and second superabsorbent and distribution layers. Any optional additional cores may be disposed on a body-facing surface of the first absorbent core or second absorbent core or on a garment-facing surface of the first absorbent core or second absorbent core.

As stated previously, in some forms, the first absorbent core layer or laminate has end edge 66 that is complementary in shape to its respective end edge 67. More specifically, the end edge 66 of the first absorbent core layer or laminate may conform shapewise to the end edge 67 of the same. The same conformance may apply to the second absorbent core layer or laminate. This conformation results from a nested cut of the first absorbent core layer or laminate and the second absorbent core layer or laminate that provides matching or shape fitting ends. Likewise, this feature may also be prevalent in any optional absorbent cores that might be incorporated into the absorbent system. This nesting or nested cut feature of the absorbent cores allow for reduced waste of trim during manufacture. It has also been found that it is possible to configure the first and second absorbent core layers or laminates in a manner that allows for their respective convex edges to oppose one another when the first and second layers are overlapped and joined forming an absorbent system with a central portion 205C comprising an overlapping area.

Referring to FIGS. 3-4B, as noted previously, the front end portion of the absorbent system 205F can be formed from end edge 66 or end edge 77 of either the first absorbent core or the second absorbent core. A rear end portion of the absorbent system 205R is similarly formed from end edge 66 or end edge 77 of the other of the first absorbent core or the second absorbent core. This configuration yields an absorbent system with matching (i.e., a male connection) ends. In other forms, a front end portion of the absorbent system may be formed from end edge 66 or end edge 76 of either the first absorbent core or the second absorbent core while the rear end portion of the absorbent system is formed from end edge 67 or end edge 77 of the other of the first absorbent core or second absorbent core. In such forms, the second end is shaped as a female connection and therefore does not match the front end portion of the same core. In other forms, the front end portion of the absorbent system may be formed from the end edge 67 of the first absorbent core or end edge 77 of the second absorbent core. A rear end portion of the absorbent system may be similarly formed from the end edge 67 of the remaining first absorbent core or the end edge 77 of the second absorbent core. This configuration yields an absorbent system with matching (i.e., a female connection) ends. It should be noted, however, that the width of the first and second absorbent cores may be the same or different as mentioned herein. The nested cuts of the end edges of each of the first and second absorbent cores can have shapes selected from the group consisting of arcs, semicircles, semi-ellipses, chevrons, rectangles, sinusoids, jigsaws, and combinations thereof.

In some forms, the first or second absorbent cores may include one or more recessed areas that run along the machine direction or cross direction. These recessed areas may coincide with the discontinuous patterns of one or more of a superabsorbent layer and distribution layer, whether it be of the first absorbent core, second absorbent core, or both. These recessed areas may also merely be formed by embossing of the first or second absorbent cores. These recessed areas may alternatively be formed by slitting, cutting, ring-rolling, or otherwise providing mechanical deformation through the first and/or second absorbent cores. Each manner of recessed area formation mentioned herein is intended to yield a recessed area that is capable of providing a point of preferential bending of the overall article.

Additionally, for those forms where the first absorbent core and/or the second absorbent core do not comprise laminate structures, an airlaid core material can be utilized. Any suitable airlaid core can be utilized. Airlaid core material can be obtained by a manufacturer of such materials or can be made online via equipment known in the art. Where an airlaid core is utilized, the need for separate superabsorbent layers and distribution layers may be reduced. In such forms, the absorbent core web 500 (shown in FIG. 5) may comprise an airlaid web as described herein. Suitable airlaid absorbent core structures are disclosed in U.S. Pat. Nos. 8,105,301 and 8,603,622 and U.S. Patent Application No. 2017/0348166.

Superabsorbent Layers

Referring to FIG. 4B, the first and second superabsorbent layers 61, 71 of the first and second absorbent core laminates 760, 770 comprise superabsorbent polymers or absorbent gelling materials (AGM). In some forms, the superabsorbent layer 61 and/or 71 may comprise the carrier web and composition. In such forms, superabsorbent may be deposited on the carrier web to form the superabsorbent layers. The superabsorbent layers may comprise AGM particles or AGM fibers. In general, such AGM's have been used only for their fluid-absorbing properties. Such materials form hydrogels on contact with liquid (e.g., with urine, blood, and the like). One highly preferred type of hydrogel-forming, absorbent gelling material is based on the hydrolyzed polyacids, especially neutralized polyacrylic acid. Hydrogel-forming polymeric materials of this type are those which, upon contact with fluids (i.e., liquids) such as water or body fluids, imbibe such fluids and thereby form hydrogels. In this manner, fluid discharged into the fluid absorbent structures herein can be acquired and held. These preferred superabsorbent polymers will generally comprise substantially water-insoluble, slightly cross-linked, partially neutralized, hydrogel-forming polymer materials prepared from polymerizable, unsaturated, acid-containing monomers.

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Fluid absorbent gelling material particles preferably have a particle size of from about 30 microns to about 2 mm for substantially all of the particles. "Particle Size" as used herein means the weighted average of the smallest dimension of the individual particles.

In some forms, the absorbent cores or portions thereof of the present disclosure may be substantially free of airfelt and are thus distinct from mixed layers that may include airfelt. As used herein, "substantially free of airfelt" means less than 5%, 3%, 1%, or even 0.5% of airfelt. In some forms, there may be no measurable airfelt in the superabsorbent layers. In the case of the first superabsorbent layer, it is preferably disposed onto the first distribution layer discontinuously. And as noted previously, the second superabsorbent layer may, in conjunction with the first superabsorbent layer or independently thereof, be disposed on the second distribution layer discontinuously. As used herein "discontinuously" or "in a discontinuous pattern" means that the superabsorbent polymers are applied onto the first distribution layer in a pattern of disconnected shaped areas. These areas of superabsorbent polymers or areas free of superabsorbent polymer may include, but are not limited to linear strips, non-linear strips, circles, rectangles, triangles, waves, mesh, and combinations thereof. The first superabsorbent layer like the second superabsorbent layer may, however, be disposed onto its respective distribution layer in a continuous pattern. As used herein "continuous pattern" or "continuously" means that the material is deposited and or secured to a superabsorbent carrier material and/or the adjacent distribution layer in an uninterrupted manner such that there is rather full coverage of the distribution layer by the superabsorbent polymer.

In some forms, the first and second superabsorbent layers may comprise superabsorbent polymers that are the same. In other embodiments, the first and second superabsorbent layers may comprise superabsorbent polymers that are different from one another. This is may be in addition to the different deposition patterns that are discussed above.

The superabsorbent layers are disposed having a thickness of 0.2 mm, 0.3 mm, 0.4 mm, or 0.5 mm to 1 mm, 1.2 mm, 1.4 mm, 1.8 mm, or 2 mm. The first and second superabsorbent layers may have the same or different cross-direction widths as applied to their respective distribution layers. For instance, the cross-direction widths of the first and second superabsorbent layers may be from 20 mm, 25 mm, 30 mm, 35 mm, or 40 mm to 50 mm, 60 mm, 65 mm, 70 mm, 80 mm, or 90 mm. Alternatively, in embodiments where the widths of the first and second superabsorbent layers differ from one another in the cross-direction width, the first superabsorbent layer may have a lesser cross-direction width than the second superabsorbent layer. In particular, the first superabsorbent layer may have a cross-direction width that is less than about 95%, 90%, 80%, 70%, or even 60% of the width of the second superabsorbent layer.

In certain embodiments, the one or both of the first and second superabsorbent layers span greater than greater than about 50%, 60%, 70%, 80%, 90%, or even 95% of the cross-direction width of a superabsorbent carrier layer and/or the respective adjoining first or second distribution layer. Forms of the present disclosure are contemplated where the absorbent core web 500 comprises a superabsorbent layer which is processed to form the superabsorbent layer 61 and superabsorbent layer 71.

Distribution Layers

The first and second distribution layers are useful for wicking bodily fluids away from the skin of a wearer to facilitate comfort of continued wear after a release. In some forms, the support web may comprise the distribution layer. In some forms, the support web may be configured similar to the carrier web described herein. In some forms, the first and second distribution layers of the first and/or second laminates not only face one another but are joined in an offset manner to form part of the core. The distribution layers comprise one or more of cellulose and commuted wood pulp. This may be in the form of airlaid. The airlaid may be chemically or thermally bonded. In particular, the airlaid may be multi bonded airlaid (MBAL). In this instance, the distribution layer may further comprise a fibrous thermoplastic adhesive material at least partially bonding the airlaid to itself and adjacent distribution layers, superabsorbent layers, or other additional (optional) layers. It should be noted that the same materials that are suitable for the optional layers of the chassis are envisioned as suitable for use in the distribution layers. The basis weight for each of the first and second distribution layers range from 80 gsm, 80 gsm, 100 gsm, 110 gsm, 120 gsm, or 130 gsm to 140 gsm, 150 gsm, 160 gsm, 180 gsm, 200 gsm, 220 gsm, or 240 gsm. A preferred basis weight is 135 gsm for each of the distribution layers of the first and second laminates.

Barrier Cuffs

Referring back to FIG. 2, the incontinence pad 10 may further comprise a first barrier cuff 230A and a second barrier cuff 230B and fastening adhesive 211 disposed on the garment-facing surface 20B of the chassis 20. As shown, the fastening adhesive 211 may not extend out laterally to the same extent as the absorbent system 205. As such, constructions where pad curl is reduced would be beneficial.

The first barrier cuff 230A and the second barrier cuff 230B may be attached to the chassis 20 in any suitable location. For example, as shown, the first barrier cuff 230A and the second barrier cuff 230B may be attached to a wearer-facing surface 20A of the chassis 20. As shown, the first barrier cuff 230A and the second barrier cuff 230B are attached to the primary topsheet 203. In some forms, the first barrier cuff 230A and the second barrier cuff 230B may attached to a garment-facing surface 20B of the chassis 20. For example, the first barrier cuff 230A and the second barrier cuff 230B may be attached to the backsheet 207.

Some examples of other suitable barrier cuffs are described in U.S. Pat. Nos. 4,695,278; 4,704,115; 4,795,454; 4,909,803; U.S. Patent Application Publication No. 2009/0312730.

As shown, in some forms, the first barrier cuff 230A comprises a first cover 231 and a first elastic member 233. The second barrier cuff 230B comprises a second cover 235 and a second elastic member 237. As shown, the first cover 231 may fully enclose the first elastic member 233. Similarly, the second cover 235 may fully enclose the second elastic member 237.

While the first barrier cuff 230A and the second barrier cuff 230B are shown as discrete elements which are attached to the chassis 20, any suitable configuration may be utilized. For example, the first cover 231 and/or the second cover 235 may comprise a portion of the primary topsheet 203 and/or a portion of the backsheet 207. In such forms, the first barrier cuff 230A and/or the second barrier cuff 230B may be integrally formed with the chassis 20. A form where the first barrier cuff 230A and the second barrier cuff 230B are integrally formed with the chassis 20 is shown in FIG. 3 and discussed hereafter.

The first elastic member 233 and the second elastic member 237 may be attached to the first cover 231 and the second cover 235, respectively, by any suitable means. In one example, the first elastic member may be adhesively attached to the first cover 231. Similarly, the second elastic member 237 may be adhesively attached to the second cover 235. For example, as shown, first adhesive portions 251 and 253 may attach the elastic members 233 and 237 to their respective covers 231 and 235. Similarly, second adhesive portions 255 and 257 may attach their respective covers 231 and 235 to the primary topsheet 203. As described below, the first elastic member 233 and the second elastic member 237 may be attached in only a portion the first cover 231 and second cover 235, respectively. Additional forms are contemplated where the first elastic member 233 and/or the second elastic member 237 are attached to the chassis 20 in conjunction with or independently from their respective covers 231 and 235.

Referring to FIG. 3, the elastic members 233 and 237 may be disposed laterally inboard of side edges 205A and 205B of the absorbent system 205. In other forms, the elastic members 233 and 237 may be disposed laterally outboard of the side edges 205A and 205B of the absorbent system 205. Still in other forms, the elastic members 233 and 237 may be disposed laterally inboard of the side edges 205A and 205B of the absorbent system 205 in the first end region 40 and the second end region 48 but laterally outboard of side edges 205A and 205B of the absorbent system 205 in the intermediate region 44. Additional forms are contemplated where the elastic members 233 and 237 are disposed laterally inboard of the side edges 205A and 205B of the absorbent system 205 in the first end region 40 but are disposed outboard of the side edges 205A and 205B of the absorbent system 205 in the intermediate region 44 and/or the second end region 48.

The elastic members comprised by the barrier cuffs can be glued in, in various glue lengths using various glues and glue amounts and placements. Placement of the glue is yet another variable which should be considered especially when designed with the core flexibility in mind. Gluing of the elastic members and the covers create anchor points on the pad.

The covers of the barrier cuffs of the present invention can be made of varying types of nonwovens of different MD and CD flexibility. The cover can be bonded to the topsheet of the absorbent article, such as, for example, by a slot coated stripe of adhesive, glue beads, ultrasonic sealing, or other suitable bonding agents. In certain forms of the present invention, the cover can be bonded to the backsheet at the side edges 22 and 24 (see FIG. 1) of the pad, such as, for example, using a crimp or other suitable bonding agents, such as, for example, adhesive.

Elastic members may comprise any suitable elastic material. Some suitable examples include Spandex™ or other similar polyurethanes, natural or synthetic rubber, styrene block copolymers, metallocene polyolefins, Lycra™, or any other suitable elastomer materials known in the art. Preferably the elastic member is durable for ease of processing and for during the use of the article and exhibits excellent elasticity (recovery after strain) even under strains as high as 400%.

Additionally, the elastic members of the present disclosure may comprise any suitable dtex. In other forms, the elastic members may comprise a dtex of 680 or less. In some forms, the elastic members may have a dtex between 680 and 470, specifically including all numbers within the range and any ranges created thereby.

Minimum spacing between the first barrier cuff 230A and the second barrier cuff 230B may be largely driven by female anatomy. However, tradeoffs can occur where the barrier cuffs (and their respective elastic members) are disposed too far outboard of the absorbent system 205 and too far inboard of the absorbent system 205. As such, spacing between the most distal elastic members of their respective barrier cuffs should be carefully selected. Starting from the narrowest width, spacing between the most distal elastic members of the first barrier cuff 230A and the second barrier cuff 230B should be large enough to allow sufficient access to the absorbent system 205 during use while also taking into account the forces which will be applied to the pad. If too narrow, access to a portion of the absorbent system 205 could be obstructed which could lead to leakage despite the barrier cuffs 230A and 230B. In some forms of the present invention, minimum spacing between the elastic member of the first barrier cuff 230A and the elastic member of the second barrier cuff 230B which are most distal to one another may be at least 20 mm. Any suitable spacing may be utilized. For example, in some forms of the present invention, the spacing may be greater than or equal to about 20 mm, greater than about 30 mm, greater than about 33 mm, greater than about 35 mm, greater than about 40 mm, greater than about 45 mm, greater than about 50 mm, greater than about 54 mm, greater than about 60 mm, greater than about 65 mm, less than or equal to about 70 mm, or less than about 65 mm, or less than about 60 mm, less than about 55 mm, less than about 50 mm, less than about 45 mm, less than about 40 mm, less than about 35 mm, less than about 30 mm, less than about 25 mm, specifically including any values within these ranges or any ranges created thereby.

Additional Features

In some forms of the present invention, the incontinence pads or sanitary napkins may comprise wings. Wings can provide additional leakage protection for the incontinence pad and can help secure the pad to the underwear of the user. Any suitable wing configuration known in the art may be utilized.

All the components can be adhered together with adhesives, including hot melt adhesives, as is known in the art. The adhesive can be Findlay H2128 UN or Savare PM 17 and can be applied using a Dynafiber HTW system.

Per FIG. 2, during use, the pad can be held in place by any support or attachment suitable for such purposes. In certain forms of the present invention, the pad is placed in the user's undergarment or panty and secured thereto by the fastening adhesive 211. The fastening adhesive 211 secures the pad in the crotch portion of the user's panty. A portion or all of the garment-facing surface 20B of the chassis 20 is coated with fastening adhesive 211. Any adhesive or glue suitable for such purposes can be used for the fastening adhesive 211 herein, such as, for example, using pressure-sensitive adhesive. Suitable adhesives include, for example, Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the absorbent article is placed in use, the pressure-sensitive adhesive is typically covered with a removable release liner in order to keep the adhesive from drying out or adhering to a surface other than the crotch portion of the panty prior to use. Suitable release liners are also described in U.S. Pat. Nos. 4,917,697 and 4,556,146. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The pad can be used by removing the release liner and thereafter placing the absorbent article in a panty so that the adhesive contacts the panty. The adhesive maintains the absorbent article in its position within the panty during use. The release liner can also be a wrapper that can individually package the pad.

Again, although the majority of discussion herein is around incontinence pads and sanitary napkins, it is envisioned that this invention is also useful for taped diapers, training pants which pull on, adult incontinence diapers and pants, and replaceable pads for incontinence and menses collection that might be inserted and removed after use in a disposable or durable panty or underpant.

Test Methods

Linear Distances

Linear distances may be measured by any appropriate instrument that is calibrated and capable of a measurement to the nearest 0.1 mm. Area measurements are made using the projected area of the article, as viewed orthogonally to the plane of the longitudinal and transverse axes, in square millimeters to the nearest 0.1 mm$^2$.

Caliper

The caliper, or thickness, of a material is measured as the distance between a reference platform on which the material rests and a pressure foot that exerts a specified amount of pressure onto the material over a specified amount of time. All measurements are performed in a laboratory maintained at 23° C.±2 C.° and 50%±2% relative humidity and test samples are conditioned in this environment for at least 2 hours prior to testing.

Caliper is measured with a manually-operated micrometer equipped with a pressure foot capable of exerting a steady pressure of 0.50 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter that is smaller than the test sample and capable of exerting the required pressure. A suitable pressure foot has a diameter of 56 mm, however a smaller or larger foot can be used depending on the size of the sample being measured. The test sample is supported by a horizontal flat reference platform that is larger than and parallel to the surface of the pressure foot. The system is calibrated and operated per the manufacturer's instructions.

Obtain a test sample by removing it from an absorbent article package. When excising the test sample from an absorbent article package, use care to not impart any contamination or distortion to the test sample layer during the process. Leave the article in its folded state for FOLDED CALIPER measurements. Unfold the article after completing the FOLDED CALIPER measurements and take UNFOLDED CALIPER measurements. The test sample must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm±1.0 mm per second until the full pressure is exerted onto the test sample. Wait 5 seconds and then record the caliper of the test sample to the nearest 0.01 mm. In like fashion, repeat for a total of five replicate test samples. Calculate the arithmetic mean for all caliper measurements and report as Thickness to the nearest 0.01 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of disposable absorbent articles, each of the absorbent articles within the array comprising a front end portion, an opposing rear end portion, and an intermediate portion disposed between the front end portion and the rear end portion, the array further comprising:
a first plurality of absorbent articles and a second plurality of absorbent articles, each of the first plurality of absorbent articles and second plurality of absorbent articles comprising: a topsheet, a backsheet, and an absorbent system disposed between the topsheet and the backsheet, the absorbent system comprising a first absorbent core and a second absorbent core, wherein the first absorbent core and the second absorbent core have equal absorbent core lengths but are disposed offset from one another such that the front end portion comprises only one of the first absorbent core or the second absorbent core and the rear end portion comprises only the other of the first absorbent core or the second absorbent core, wherein the front end portion and the rear end portion have equal front end portion and rear end portion lengths, wherein a central portion is disposed between the front end portion and the rear end portion;
wherein the absorbent system of the first plurality of absorbent articles comprises the central portion having a first length and the absorbent system of the second plurality of absorbent articles comprises the central portion having a second length, wherein the second length is greater than the first length, and wherein the first plurality of absorbent articles comprises a first folded caliper and the second plurality of absorbent articles comprises a second folded caliper, wherein the second caliper is greater than the first caliper.

2. The array of claim 1, wherein each of the first plurality of absorbent articles and second plurality of absorbent articles comprise a pair of fold lines, wherein at least one of the fold lines is disposed in the central portion.

3. The array of claim 2, wherein a ratio of the second folded caliper to the first folded caliper is from about 2.0 to greater than 1.0.

4. The array of claim 2, wherein a ratio of the second folded caliper to the first folded caliper is from about 1.8 to greater than 1.0.

5. The array of claim 2, wherein a ratio of the second folded caliper to the first folded caliper is from about 1.5 to greater than 1.0.

6. The array of claim 2, wherein a ratio of the second folded caliper to the first folded caliper is from about 1.4 to greater than 1.0.

7. The array of claim 2, wherein a ratio of the second folded caliper to the first folded caliper is from about 1.2 to greater than 1.0.

8. The array of claim 7, wherein both fold lines are disposed in the central portion.

9. The array of claim 1, wherein each of the first plurality of absorbent articles and second plurality of absorbent articles comprise a pair of fold lines, wherein the fold lines are disposed outboard of the central portion.

10. The array of claim 9, wherein a ratio of the second folded caliper to the first folded caliper is from about 1.6 to greater than 1.0.

11. The array of claim 9, wherein a ratio of the second folded caliper to the first folded caliper is from about 1.4 to greater than 1.0.

12. The array of claim 9, wherein a ratio of the second folded caliper to the first folded caliper is from about 1.2 to greater than 1.0.

13. The array of claim 9, wherein a ratio of the second folded caliper to the first folded caliper is from about 1.1 to greater than 1.0.

14. The array of claim 1, wherein the first plurality of absorbent articles and second plurality of absorbent articles comprise a pair of fold lines, wherein the fold lines for the first plurality of absorbent articles are disposed outboard of the central portion, and wherein the fold lines for the second plurality of absorbent articles are disposed within the central portion.

15. The array of claim 14, wherein a ratio of the second folded caliper to the first folded caliper is from about 2.5 to greater than 1.0.

16. The array of claim 14, wherein a ratio of the second folded caliper to the first folded caliper is from about 2.0 to greater than 1.0.

17. The array of claim 14, wherein a ratio of the second folded caliper to the first folded caliper is from about 1.6 to greater than 1.0.

18. The array of claim 14, wherein the second plurality of articles have a higher capacity than the first plurality of articles.

* * * * *